United States Patent [19]

Beuther et al.

[11] Patent Number: 4,585,798

[45] Date of Patent: Apr. 29, 1986

[54] SYNTHESIS GAS CONVERSION USING RUTHENIUM-PROMOTED COBALT CATALYST

[75] Inventors: Harold Beuther, Vero Beach, Fla.; Thaddeus P. Kobylinski, Prospect, Pa.; Charles L. Kibby, Gibsonia, Pa.; Richard B. Pannell, Allison Park, Pa.

[73] Assignee: Gulf Research & Development Company, Pittsburgh, Pa.

[21] Appl. No.: 635,911

[22] Filed: Jul. 30, 1984

Related U.S. Application Data

[60] Continuation-in-part of Ser. No. 310,969, Oct. 13, 1981, abandoned, and a continuation-in-part of Ser. No. 540,662, Oct. 11, 1983, Pat. No. 4,493,905, which is a division of Ser. No. 310,977, Oct. 13, 1981, Pat. No. 4,413,064.

[51] Int. Cl.$^4$ .............................................. C07L 1/04
[52] U.S. Cl. .................................. 518/715; 518/700; /32
[58] Field of Search ..................... 518/715, 716, 700

[56] References Cited

U.S. PATENT DOCUMENTS

| | | |
|---|---|---|
| 3,829,515 | 8/1974 | Zuech et al. . |
| 3,880,929 | 4/1975 | Drake . |
| 3,896,173 | 7/1975 | Drake . |
| 3,896,174 | 7/1975 | Drake . |
| 3,898,286 | 8/1975 | Drake . |
| 3,912,787 | 10/1975 | Nowack et al. . |
| 3,962,337 | 6/1976 | Drake . |
| 3,988,344 | 10/1976 | Finch et al. . |
| 3,989,759 | 11/1976 | Yoo . |
| 4,042,614 | 8/1977 | Vannice et al. . |
| 4,053,515 | 10/1977 | Drake . |
| 4,088,671 | 5/1978 | Kobylinski . |
| 4,101,450 | 7/1978 | Hwang et al. . |
| 4,136,104 | 1/1979 | Hwang et al. . |
| 4,157,338 | 6/1979 | Haag et al. . |
| 4,171,320 | 10/1979 | Vannice et al. . |
| 4,215,019 | 7/1980 | Drake et al. . |
| 4,233,466 | 11/1980 | Fiato . |
| 4,243,610 | 1/1981 | Drake et al. . |
| 4,268,689 | 5/1981 | Knifton . |
| 4,399,234 | 8/1983 | Beuther et al. ............... 518/715 |
| 4,433,178 | 2/1984 | Lin et al. . |
| 4,492,774 | 1/1985 | Kibby et al. . |

FOREIGN PATENT DOCUMENTS

2024246A 1/1980 United Kingdom .

OTHER PUBLICATIONS

"Proceedings of the Canadian Symposium on Catalysis," Kibby et al., (Preprint), 1981.
Pannell et al., Seventh International Congress on Catalysis, Jun. 30, 1980, pp. 447–459.

*Primary Examiner*—Howard T. Mars
*Attorney, Agent, or Firm*—Roylance, Abrams, Berdo & Goodman

[57] ABSTRACT

Synthesis gas comprising carbon monoxide and hydrogen is converted to a liquid hydrocarbon by contacting the synthesis gas under conversion conditions with a supported cobalt-ruthenium catalyst in which the cobalt to ruthenium molar ratio is greater than about 200:1. The catalyst is preferably prepared by using a non-aqueous impregnation solution and using an activation procedure involving reduction, oxidation and reduction.

18 Claims, No Drawings

SYNTHESIS GAS CONVERSION USING RUTHENIUM-PROMOTED COBALT CATALYST

CROSS-REFERENCE TO RELATED APPLICATIONS

This application is a continuation-in-part of U.S. Ser. No. 310,969 filed Oct. 13, 1981 now abandoned and U.S. Ser. No. 540,662 filed Oct. 11, 1983, now U.S. Pat. No. 4493905 which, in turn, is a divisional of U.S. Ser. No. 310,977 filed Oct. 13, 1981, now U.S. Pat. No. 4,413,064, all in the name of H. Beuther et al.

FIELD OF THE INVENTION

The present invention relates to a process for the conversion of synthesis gas to liquid hydrocarbons in the presence of a catalyst containing cobalt and ruthenium, to the catalyst, per se, and the preparation of such catalyst. More particularly, this invention relates to the conversion of synthesis gas to liquid hydrocarbons using a cobalt-ruthenium catalyst containing very low levels of ruthenium as compared to cobalt.

BACKGROUND INFORMATION

The growing importance of alternative energy sources has brought a renewed interest in the Fischer-Tropsch synthesis as one of the more attractive direct and environmentally acceptable paths to high quality transportation fuels. The Fischer-Tropsch synthesis involves the production of hydrocarbons by the catalyzed reaction of CO and hydrogen. Commercial plants have operated in Germany, South Africa and other parts of the world based on the use of particular catalysts. The German commercial operation, for example, concentrated on the use of a precipitated cobalt-thoria-kieselguhr fixed-bed catalyst, and a later modification where MgO, for economy reasons, replaced part of the thoria.

More recently, U.S. Pat. No. 4,088,671 to T. P. Kobylinski describes the use of a ruthenium-promoted cobalt catalyst on a support, such as alumina or kieselguhr, in the synthesis of hydrocarbons from the reaction of CO and hydrogen at substantially atmospheric pressure. The patent discloses that the molar ratio of cobalt to ruthenium in the finished catalyst can suitably be from 5:1 to about 200:1, is more usually 10:1 to 100:1, and most usually it is from 15:1 to 80:1. As ruthenium is expensive, the patent indicates that it is preferred to employ ruthenium in the minimum amount necessary to achieve the desired result (column 2, lines 60–67). The minimum amount of ruthenium disclosed in relation to cobalt is a molar ratio of cobalt to ruthenium of 200:1 (column 2, line 62). Further, the patent indicates that the method employed to deposit the catalytic materials is not critical, but discloses the use of aqueous solutions of metal salts to prepare the catalyst (column 3, lines 27-38).

SUMMARY OF THE INVENTION

It has now been found in accordance with the present invention, that synthesis gas comprising hydrogen and carbon monoxide can be selectively converted under synthesis gas conversion conditions to liquid hydrocarbons using a supported cobalt-ruthenium catalyst containing from about 5 to about 30 weight percent cobalt in which the molar ratio of cobalt to ruthenium is greater than about 200:1 and up to about 3400:1. Surprisingly, it has been discovered that the molar ratio of cobalt to ruthenium can be significantly increased above the 200:1 level and still provide a catalyst having in excess of 100 percent activity for synthesis gas conversion over that achieved without the ruthenium. Moreover, as will be hereinafter demonstrated, under higher pressure reaction conditions, a catalyst having a cobalt to ruthenium molar ratio greater than 200:1 can have a greater activity than a similar catalyst having a cobalt:ruthenium ratio below 200:1.

According to a preferred embodiment of the invention, it was further discovered that if the supported cobalt-ruthenium catalyst of the present invention is prepared using an impregnation solution consisting essentially of a non-aqueous, organic solvent for depositing the cobalt and ruthenium onto the support, the resulting catalyst can achieve a greater activity for synthesis gas conversion than is achieved by the same catalyst prepared using the conventional precipitation from aqueous solution method for depositing the metals on the catalyst support.

According to still another preferred embodiment of the present invention, it has been found that catalyst activity for synthesis gas conversion can be increased even further by preparing the catalyst using an activation procedure in which the impregnated catalyst is subjected to the steps of (i) reduction, (ii) oxidation, and (iii) reduction herein termed "ROR activation". Surprisingly, it was found that the use of such ROR activation produces a catalyst that can achieve a greater activity for synthesis gas conversion at a cobalt to ruthenium ratio far above 200:1 than can the same catalyst having a cobalt to ruthenium ratio below 200:1, but prepared without ROR activation.

According to another preferred embodiment, the synthesis gas conversion process of the present invention is conducted under pressures of at least 50 pounds per square inch (3.4 atmospheres). Surprisingly, it was found that the use of the low ruthenium catalysts of the present invention under higher pressures results in activities greater than that achievable with larger quantities of ruthenium at the same pressure.

DESCRIPTION OF THE PREFERRED EMBODIMENTS

The catalyst of the present invention consists essentially of cobalt and ruthenium, which, preferably, can be additionally promoted with a metal oxide, such as lanthanum oxide, and is supported on a refractory oxide, in particular on gamma or etaalumina or mixtures thereof having low acidity, high surface area and high purity. The catalyst contains from about 5 to about 30 weight percent cobalt based upon total catalyst weight, preferably from about 8 to about 25 weight percent cobalt, with from about 10 to about 20 weight percent being especially preferred.

The amount of ruthenium utilized is much smaller than that previously considered to be necessary in order to significantly enhance the activity of the cobalt catalyst. Accordingly, the ratio of cobalt to ruthenium is greater than about 200:1 up to about 3400:1, preferably from about 250:1 to about 1000:1. However, for optimum improvement in catalyst activity at minimum catalyst costs, it is especially preferred that the cobalt to ruthenium molar ratio not exceed about 300:1 to about 700:1.

In order to obtain a significant benefit from ruthenium, the amount of ruthenium should be from about 0.01 to about 0.50 weight percent, preferably from about 0.05 to about 0.25 weight percent based upon total catalyst weight.

In addition to cobalt and ruthenium, the catalyst preferably contains from about 0.1 to 5 weight percent, preferably from about 0.1 to about 2 weight percent of a suitable promoter metal oxide, such as a Group IIIB or IVB metal oxide. Oxides of the actinides and lanthanides are preferred, and, thus, suitable metal oxides include, for example, $Sc_2O_3$, $Y_2O_3$, $Ac_2O_3$, $Pr_2O_3$, $PrO_2$, $Nd_2O_3$, $Sm_2O_3$, $Eu_2O_3$, $Gd_2O_3$, $Tb_2O_3$, $Tb_4O_7$, $Dy_2O_3$, $Ho_2O_3$, $Er_2O_3$, $Tm_2O_3$, $Yb_2O_3$, $Lu_2O_3$, $UO_2$, $UO_3$, $U_3O_8$, and the like. Especially preferred metal oxides for inclusion in the catalyst of the present invention include $La_2O_3$, $CeO_2$, $ZrO_2$, $TiO_2$, $HfO_2$, $ThO_2$, and unseparated rare earth oxide mixtures high in lanthanum, praseodymium, and neodymium. Other preferred promoters include $MnO_2$ and $MgO$. It is believed that such metal oxides affect product distribution and help direct the synthesis reaction to provide liquid hydrocarbons by controlling residual catalyst impurities and/or the acid sites on the support. Thus, such promoter metals can be omitted by merely omitting them from the impregnation solution, and the resulting catalyst is still operative.

The cobalt and promoter metals can be supported on any suitable support. Preferably, the support is an extruded alumina support which is composed of gamma-alumina, eta-alumina or mixtures thereof is present in an amount of from about 200 to about 2000 parts by weight alumina per 100 parts by weight of cobalt, preferably between about 300 and about 1250 parts of alumina per 100 parts of cobalt, with from about 400 to about 900 parts by weight of alumina per 100 parts by weight cobalt being especially preferred. Pure gamma-alumina is preferred.

The alumina support of the present invention is characterized as having low acidity, a high surface area and high purity. The expression "low acidity" as used in the present application means that the alumina support has a Brønsted activity with $H_o<1.5$ which is less than 5 micromol per gram or about $10^{16}$ acid sites per square meter of surface area. The low acidity of the support is required in order to enable the catalyst to provide a high molecular weight hydrocarbon product boiling in the diesel fuel range.

The surface area of the alumina support of the present invention is at least 40 or 50 square meters per gram but is not so great as to become unduly microporous so as to permit reactant materials to enter the interstices of the catalyst. A suitable surface area is from about 40 to about 250, preferably from about 150 to about 225 square meters per gram.

As indicated, the catalyst support of the present invention must be of high purity. The expression "high purity" as used in the present application means that the catalyst contains negligible amounts of sulfur, silicon, phosphorous or other material having a deleterious effect on the metal dispersion or the production of high molecular weight hydrocarbon products. For sulfur, the impurity levels should be below 0.1 weight percent, preferably below 0.02 weight percent, and especially below 0.01 weight percent. For impurities creating acid sites, less than 5 micromol per gram should be present (about 0.01–0.1 weight percent depending on molecular weight). The deleterious effect of acidity is isomerization and cracking of intermediate olefins, removing them from chain growth and producing a low molecular weight product.

The method employed to deposit the catalytic metals of the present invention onto the alumina support involves the use of a nonaqueous, organic impregnation solution consisting essentially of soluble cobalt and ruthenium salts and a soluble promoter metal salt i.e., lanthanum salt, in order to achieve the necessary metal loading and distribution required to provide the highly selective and active catalyst of the present invention.

Initially, the alumina support is treated by oxidative calcination of the gamma and/or eta-alumina at a temperature in the range of from about 450° to about 900° C., preferably from about 600° to about 750° C. to remove water from the micropores of the support.

Meanwhile, a non-aqueous organic solvent solution of cobalt, ruthenium and lanthanum salts, for example, is prepared. The non-aqueous organic solvent of the present invention is a non-acidic liquid which is formed from moieties selected from the group consisting of carbon, oxygen, hydrogen and nitrogen, and possesses a relative volatility of at least 0.1. The expression "relative volatility" as used in the present application is defined as the ratio of the vapor pressure of the solvent to the vapor pressure of acetone, as reference, when measured at 25° C.

Suitable solvents include, for example, ketones, such as acetone, butanone (methyl ethyl ketone); the lower alcohols, e.g., methanol, ethanol, propanol and the like; amides, such as dimethyl formamide; amines, such as butylamine; ethers, such as diethylether and tetrahydrofuran; hydrocarbons, such as pentane and hexane; and mixtures of the foregoing solvents. The preferred solvents of the present invention are acetone, for cobalt nitrate, or tetrahydrofuran, for cobalt carbonyl.

The amount of solvent utilized is an amount that is at least equivalent to the pore volume of the alumina utilized, but not greater than five times the alumina pore volume. For example, a commercially available gamma-alumina useful in the present invention has a pore volume of between about 0.2 to about 0.7 cubic centimeters pore volume per gram of alumina.

Suitable cobalt salts include, for example, cobalt nitrate, cobalt acetate, cobalt carbonyl, cobalt acetylacetonate, or the like with cobalt nitrate and cobalt carbonyl [$Co_2(CO)_8$] being especially preferred. Likewise, any suitable ruthenium salt, such as ruthenium nitrate, chloride, acetate or the like can be used. Ruthenium acetylacetonate is preferred. In addition, any suitable promoter metal, e.g., lanthanum salt, such as lanthanum nitrate, lanthanum acetate or the like can be employed. In general, any metal salt which is soluble in the organic solvent of the present invention and will not introduce acidity or have a poisonous effect on the catalyst can be utilized.

The calcined alumina support is then impregnated in a dehydrated state with the non-aqueous, organic solvent solution of the metal salts. Thus, the calcined alumina should not be unduly exposed to atmospheric humidity so as to become rehydrated.

Any suitable impregnation technique can be employed including techniques well known to those skilled in the art so as to distend the catalytic metals in a uniform thin layer on the catalyst support. For example, the cobalt and thoria can be deposited on the support material by the "incipient wetness" technique. Such technique is well known and requires that the volume of impregnating solution be predetermined so as to provide the minimum volume which will just wet the entire surface of the support, with no excess liquid. Alternatively, the excess solution technique can be utilized if desired. If the excess solution technique is utilized, then the excess solvent present, e.g., acetone, is merely removed by evaporation. Thus, the impregnation solution can be added in excess, namely, up to five times the pore volume of the alumina, or can be added using just enough solution to fill the pore volume of the alumina.

Next, the impregnation solution and alumina are stirred while evaporating the solvent at a temperature of from about 25° to about 50° C. until "dryness".

The impregnated catalyst is slowly dried at a temperature of from about 110° to about 120° C. for a period of about 1 hour so as to spread the metals over the entire support. The drying step is conducted at a very slow rate in air.

The dried catalyst is calcined by heating slowly in flowing air, for example 10 cc/gram/minute, to a temperature in the range of from about 200° to about 400° C., preferably from about 250° to about 300° C., that is sufficient to decompose the metal salts and fix the metals. The aforesaid drying and calcination steps can be done separately or can be combined. However, calcination should be conducted by using a slow heating rate of, for example, 0.5° to about 3° C. per minute, preferably from about 0.5° to about 1° C. per minute and the catalyst should be held at the maximum temperature for a period of about 1 to about 20 hours, preferably for about 2 hours.

The foregoing impregnation steps are repeated with additional impregnation solutions in order to obtain the desired metal loading. Ruthenium and other promoter metal oxides are conveniently added together with cobalt, but they may be added in other impregnation steps, separately or in combination, either before, after, or between impregnations of cobalt. After the last impregnation sequence, the loaded catalyst support is then subjected to an activation treatment, preferably the reduction-oxidation-reduction activation treatment (ROR activation).

The impregnated catalyst is preferably slowly reduced in the presence of hydrogen. The reduction is best conducted in two steps wherein the first reduction heating step is carried out at a slow heating rate of no more than from about 0.5° to about 5° C. per minute, preferably from about 0.5° to about 1° C. per minute up to a maximum hold temperature of 200° to about 300° C., preferably 200° to about 250° C., for a hold time of from about 6 to about 24 hours, preferably from about 16 to about 24 hours under ambient pressure conditions. In the second reduction heating step, the catalyst can be heated at from about 0.5° to about 3° C. per minute, preferably from about 0.5° to about 1° C. per minute to a maximum hold temperature of from about 250° or 300° up to about 450° C., preferably from about 350° to about 400° C. for a hold time of 6 to about 65 hours, preferably from about 16 to about 24 hours. Although pure hydrogen can be employed for this reduction step, a mixture of hydrogen and nitrogen can be utilized in order to slowly reduce the catalyst. For example, the reduction step can be conducted initially using a gaseous mixture comprising 5% hydrogen and 95% nitrogen, and thereafter, the concentration of hydrogen can be gradually increased until pure hydrogen is obtained so as to slowly reduce the catalyst. Such slow reduction is particularly desirable when the metal salts utilized in the impregnation step are nitrates so as to avoid the dangers involved with an exothermic reaction in which nitrates are given off. Thus, the slow reduction may involve the use of a mixture of hydrogen and nitrogen at 100° C. for about one hour; increasing the temperature 0.5° C. per minute until a temperature of 200° C.; holding that temperature for approximately 30 minutes; and then increasing the temperature 1° C. per minute until a temperature of 350° C. is reached and then continuing the reduction for approximately 16 hours. Reduction should be conducted slowly enough and the flow of the reducing gas maintained high enough to maintain the partial pressure of water in the offgas below 1 percent, so as to avoid excessive steaming of the exit end of the catalyst bed.

The reduced catalyst is passivated by flowing diluted air over the catalyst slowly enough so that a controlled exotherm passes through the catalyst bed. After passivation, the catalyst is heated slowly in diluted air to a temperature of from about 300° to about 350° C. in the same manner as previously described in connection with calcination of the catalyst.

Next, the oxidized catalyst is then slowly reduced in the presence of hydrogen in the same manner as previously described in connection with reduction of the impregnated catalyst.

Preferably, the composite catalyst of the present invention has an average particle diameter, which depends upon the type of reactor to be utilized, of from about 0.01 to about 6 millimeters; preferably from about 1 to about 6 millimeters for a fixed bed; and preferably from about 0.01 to about 0.11 millimeters being preferred for a reactor with the catalyst suspended by gas, liquid, or gas-liquid media (e.g., fluidized beds, slurries, or ebullating beds).

The charge stock used in the process of this invention is a mixture of CO and hydrogen. Any suitable source of the CO and hydrogen can be used. The charge stock can be obtained, for example, by (i) the oxidation of coal or other forms of carbon with scrubbing or other forms of purification to yield the desired mixture of CO and $H_2$ or (ii) the reforming of natural gas. $CO_2$ is not a desirable component of the charge stocks for use in the process of this invention, but it may be present as a diluent gas. Sulfur compounds in any form are deleterious to the life of the catalyst and should be removed from the $CO-H_2$ mixture and from any diluent gases.

The reaction temperature is suitably from about 160° to about 350° C., preferably from about 175° to about 275° C., and most preferably from about 185° to about 250° C. The total pressure is, for example, from about 1 to about 100 atmosphere, preferably from about 3 to about 35 atmospheres, and most preferably from about 10 to about 20 atmospheres. Surprisingly, it has been found that the use of pressures of at least 50 psi (3.4 atmospheres) using the low ruthenium catalysts of the present invention results in activities greater than that achievable with larger quantities of ruthenium at the same pressure.

The gaseous hourly space velocity based upon the total amount of feed is less than 20,000 volumes of gas per volume of catalyst per hour, preferably from about 100 to about 5000 v/v/hour, with from about 1000 to about 2500 v/v/hour being especially preferred. If desired, pure synthesis gas can be employed or, alternatively, an inert diluent, such as nitrogen, $CO_2$, methane, steam or the like can be added. As used herein, the expression "inert diluent" indicates that the diluent is non-reactive under the reaction conditions herein disclosed or is a normal reaction product.

The synthesis gas reaction using the catalysts of this invention can occur in a fixed, fluid or moving bed type of operation.

The invention will be further described with reference to the following experimental work.

EXAMPLE 1

The preparation of the catalysts used in the following experiments is exemplified by the following description of the preparation of the catalyst containing 0.05 weight percent ruthenium. The support was 70 grams of extrudate of a gamma-alumina (Ketjen CK-300 commercially available from Akzo Chemie) which had been ground and sieved to 16-30 mesh size (0.589-1.168 mm) and heated in air at 750° C. for 16 hours. Separate portions comprising 0.1680 gram of ruthenium acetylacetonate, 2336 grams of lanthanum nitrate, [La(NO$_3$)$_3$.6H$_2$O], and 87.563 grams of cobalt nitrate, [Co(NO$_3$)$_2$.6H$_2$O], were dissolved in 181 cubic centimeters of acetone. The solution was divided into three equal parts and the alumina was contacted with the first portion of the catalyst solution with stirring. Solvent was removed from the impregnated alumina in a rotary evaporator at 40° C. The dried material was then calcined in air at 300° C. for two hours. The calcined catalyst was then impregnated with the second portion of the catalyst solution and the drying and calcining steps were repeated. The calcined catalyst was then impregnated, dried, and calcined as before for a third time. The catalyst analyzed 20.00 weight percent cobalt, 1.00 weight percent lanthanum oxide, 0.05 weight percent ruthenium, and the remainder alumina.

The catalyst was divided into separate portions with the first portion (A) being reduced by passing hydrogen over the catalyst at the rate of 840 cubic centimeters per gram per hour while heating at the rate of 1° C. per minute until the catalyst reached 350° C. at which temperature the catalyst is held for six hours. A separate portion of the catalyst (B) is reduced in hydrogen flowing at the rate of 3500 cubic centimeters per gram per hour while being heated to 110° C. at the rate of 10° C. per minute. The catalyst was held at 110° C. for a period of one hour and then heated to 200° C. at the rate of 0.5° C. per minute, held for two hours, and then heated to 350° C. at the rate of 1° C. per minute and held at 350° C. for 10 hours. Next, passivation of the catalyst is conducted in flowing air, and then the catalyst is reduced once again by passing hydrogen at the rate of 840 cubic centimeters per gram per hour while heating at a rate of 1° C. per minute until the temperature of 350° C. is reached and then holding at that temperature for six hours.

A third sample of the catalyst (C) is reduced in 4800 cubic centimeters per gram per hour of hydrogen while heating at the rate of 1° C. per minute to a temperature of 350° C. for a period of fifteen hours. A fourth sample (D) is reduced by passing 4800 cubic centimeters per gram per hour of hydrogen over the catalyst sample while heating at a temperature of 1° C. per minute until a temperature of 350° C. is reached and then that temperature is maintained for fifteen hours. Next, the reduced catalyst is subjected to passivation and then is oxidized in air at 300° C. for sixteen hours. The oxidized catalyst is then reduced once again by flowing 4800 cubic centimeters per gram per hour of hydrogen while heating at the rate of 1° C. per minute until the temperature of 350° C. is reached and then held for fifteen hours.

The foregoing preparation and activation procedures were repeated, with the exception that the ruthenium content was varied to provide catalyst samples containing 0.10, 0.50 and 1.00 weight percent ruthenium.

Meanwhile, for comparative purposes, a catalyst substantially identical to the foregoing catalyst was prepared, with the exception that the ruthenium was omitted. The ruthenium-free catalyst was prepared by utilizing a gamma-alumina extrudate (Ketjen C-300) that had been ground and sieved to 16-40 mesh and calcined at 750° C. An impregnation solution was prepared by dissolving 1.59 grams of lanthanum nitrate, [La(NO$_3$)$_3$.6H$_2$O], and 59.28 grams of cobalt nitrate, [Co(NO$_3$)$_2$.6H$_2$O], in 120 cubic centimeters of acetone. The impregnation solution was divided into three equal parts and 47.40 grams of the alumina support was saturated with the first portion of the impregnation solution. The solvent was removed in a rotary evaporator at 40° C., and then calcined in air at 300° C. for two hours. The second portion of impregnation solution is added to the calcined catalyst, evacuated to dryness at 40° C. for one hour and then calcined at 300° C. in air for two hours. The third portion of the catalyst solution is added, and once again, the impregnated catalyst is evacuated to dryness at 40° C. for one hour and calcined at 300° C. in air for two hours. Next, separate samples of the impregnated catalyst are subjected to activation as previously described in connection with the ruthenium-containing catalyst utilizing the type A-D activation treatments.

A series of tests were conducted to evaluate the effect of minute amounts ruthenium as compared with cobalt upon activity of the catalyst in converting synthesis gas to hydrocarbons. In each test, synthesis gas containing 35 weight percent carbon monoxide and 65 weight percent hydrogen were passed over the catalyst sample under a pressure of 1 atmosphere. The samples activated by procedures A and B were tested at a synthesis gas flow rate of 840 cubic centimeters per gram of catalyst per hour for a period of 10-20 hours onstream, while the catalysts activated using procedures C and D were tested using 1680 cubic centimeters of synthesis gas per gram of catalyst per hour for 10-20 hours onstream.

The results of the tests are set forth in Table I, below:

TABLE I

| Test No. | Ru (Wt. %) | Co/Ru Ratio (Wt.) | Co/Ru Ratio (Molar) | CO Conversion Rate (cc/gram/hour) (A) | (B) | (C) | (D) |
|---|---|---|---|---|---|---|---|
| 1 | 0.0 | — | — | 24 | 36 | 49 | 67 |
| 2 | 0.05 | 400 | 693 | 62 | 91 | 102 | 145 |
| 3 | 0.10 | 200 | 346 | 70 | 99 | 118 | 159 |
| 4 | 0.50 | 40 | 69 | 113 | 131 | 137 | 186 |
| 5 | 1.00 | 20 | 35 | 120 | — | 131 | 194 |

As can be seen from the results in Table I (Test Nos. 2-5), the use of ruthenium significantly improved catalyst activity as compared with those tests in which no ruthenium was present (Test No. 1). Moreover, of particular significance is the fact that even when the Co/Ru molar ratio exceeded 200/1, namely in Tests 2 and 3, the catalyst activity increased in excess of 100 percent over that in which ruthenium was absent.

Additionally, it is seen from Test 3, using ROR activation procedure (D) provided catalyst activity (159 cc/g/h), which was greater than that achieved in Test 4 (C), namely 137 cc/g/h using five times the amount of ruthenium (0.10 vs. 0.50) at a Co/Ru molar ratio of 69 but without such ROR activation.

EXAMPLE 2

In order to demonstrate the effect of higher pressures, the catalyst prepared as in Example 1 and containing 20 weight percent cobalt, 1 weight percent lanthanum oxide and varying amounts of ruthenium was impregnated as described in Example 1, and activated by reducing the impregnated catalyst in hydrogen flowing at 2400 cubic centimeters per gram per hour under a pressure of approximately 1 atmosphere by slowly heating the catalyst over a five hour period to 300° C. and holding the catalyst at 300° C. for sixteen hours.

Samples of the catalyst were tested for activity under a total pressure of 240 psi (14 atmospheres). The catalyst samples were tested using synthesis gas containing a hydrogen to carbon monoxide ratio of 2 to 1 at a temperature of 185° C. while using a synthesis gas flow rate of 1166 cubic centimeters per gram per hour (test conditions A); a hydrogen to carbon monoxide ratio of 3 to 2 at a temperature of 195° C. at a rate of 1458 cubic centimeters per gram per hour (test conditions B); and a hydrogen to carbon monoxide ratio of 2 to 1 at a temperature of 195° C. at a fow rate of 1749 cubic centimeters per gram per hour (test conditions C), all tests being conducted for more than 24 hours onstream.

The tests results are set forth below in Table II:

TABLE II

| Test No. | Ru (Wt. %) | Co/Ru Ratio (Wt.) | Co/Ru Ratio (Molar) | CO Conversion Rate (cc/gram/hour) (A) | (B) | (C) |
| --- | --- | --- | --- | --- | --- | --- |
| 1 | 0.0 | — | — | 53 | 79 | 86 |
| 2 | 0.05 | 400 | 693 | 209 | 238 | 336 |
| 3 | 0.10 | 200 | 346 | 187 | 253 | 355 |
| 4 | 0.50 | 40 | 69 | 179 | 247 | 344 |
| 5 | 1.00 | 20 | 35 | 169 | 255 | 320 |

The tests results in Table II indicate that the activity of the catalyst containing very small amounts of ruthenium has roughly the same activity or better than catalysts containing much larger amounts of ruthenium. It was quite unexpected that catalysts containing a Co/Ru molar ratio greater than 200 to 1, would have an activity comparable to an identical catalyst containing much larger amounts of ruthenium as compared to cobalt.

EXAMPLE 3

The following example demonstrates the improved activity of the catalyst of the present invention when prepared using a non-aqueous impregnation solution (I) as compared to the conventional aqueous type precipitation method for preparing a cobalt catalyst.

The catalysts were impregnated in the manner described in Example 1 and contain 20 weight percent, 1 weight percent lanthanum oxide with the ruthenium being varied. Following the use of a non-aqueous impregnation solution, the catalyst is activated by reduction in hydrogen using a hydrogen flow rate of 4800 cc/g/h while being heated at the rate of 1° C. per minute to a temperature of 350° C. and then held at 350° C. for a period of fifteen hours (activation A). Other samples of the catalyst prepared by aqueous impregnation are subjected to the reduction treatment described in connection with activation procedure A, and are then subjected to passivation in air and oxidation of the catalyst while heating to a temperature of 300° C. and holding for a period of sixteen hours. The catalyst is then reduced once again using activation procedure A, this reduction, oxidation, reduction procedure being termed treatment B.

Meanwhile, a similar catalyst is prepared by aqueous precipitation (P) containing 20 weight percent cobalt, 1 weight percent lanthanum oxide with the amount of ruthenium being varied using the procedure described in U.S. Pat. No. 4,088,671 to T. P. Kobylinski, in which 125.8 grams of cobalt nitrate, $[Co(NO_3)_2.6H_2O]$, 1.32 grams of ruthenium chloride, $[RuCl_3]$, and 3.38 grams of lanthanum nitrate, $[La(NO_3)_3.6H_2O]$ were dissolved in 1300 cubic centimeters of distilled water. A second solution was prepared by dissolving 85.5 grams of $K_2CO_3$ in 1300 cubic centimeters of distilled water. The two solutions were separately heated to boiling, and then both solutions were added rapidly with vigorous stirring to 500 cubic centimeters of boiling distilled water, and immediately thereafter 100 grams of 100 mesh gamma-alumina were admixed with stirring and the stirring was continued for 10 minutes. The $K_2CO_3$ coprecipitates the metals as carbonates onto the alumina support. The resultant mixture was filtered rapidly and the precipitate was washed with distilled water until there was no evidence of potassium or nitrates remaining. The precipitate was then dried at 120° C. for 16 hours and then calcined at 350° C. for 16 hours in air. The catalyst was then activated using activating treatments A and B as previously described in connection with the catalysts of the present invention using a non-aqueous impregnation solution.

The resulting precipitated (P) and impregnated (I) catalysts were then tested for activity by contact with synthesis gas containing 35 weight percent carbon monoxide and 65 weight percent hydrogen at a temperature of 185° C. under 1 atmosphere total pressure at a synthesis gas flow rate of 1680 cc/g/h for a period of 10–20 hours onstream.

The results are set forth below in Table III:

TABLE III

| Test No. | Co (Wt. %) | Ru (Wt. %) | Co/Ru Ratio (Wt.) | Co/Ru Ratio (Molar) | Type | CO Conversion Rate (cc/g/h) (A) | (B) | CH4 (Wt. %) (A) | (B) |
| --- | --- | --- | --- | --- | --- | --- | --- | --- | --- |
| 1 | 20 | 0.0 | — | — | P | 19 | 40 | 12.0 | 8.0 |
| 2 | 20 | 0.0 | — | — | I | 49 | 67 | 7.9 | 7.3 |
| 3 | 20 | 0.05 | 400 | 693 | P | 42 | 56 | 8.2 | 7.7 |
| 4 | 20 | 0.05 | 400 | 693 | I | 102 | 145 | 7.9 | 7.6 |
| 5 | 20 | 0.15 | 133 | 231 | P | 51 | 70 | 9.1 | 8.3 |
| 6 | 20 | 0.10 | 200 | 347 | I | 118 | 159 | 7.7 | 7.5 |
| 7 | 20 | 0.50 | 40 | 69 | P | 73 | 114 | 10.2 | 8.6 |
| 8 | 20 | 0.50 | 40 | 69 | I | 137 | 193 | 8.6 | 8.1 |

TABLE III-continued

| Test No. | Co (Wt. %) | Ru (Wt. %) | Co/Ru Ratio (Wt.) | Co/Ru Ratio (Molar) | Type | CO Conversion Rate (cc/g/h) (A) | CO Conversion Rate (cc/g/h) (B) | CH$_4$ (Wt. %) (A) | CH$_4$ (Wt. %) (B) |
|---|---|---|---|---|---|---|---|---|---|
| 9 | 20 | 1.00 | 20 | 35 | I | 131 | 194 | 8.3 | 7.9 |

The results set forth in Table III demonstrate that in each case the use of a non-aqueous impregnation solution (I) for preparing the catalyst provided a catalyst having greater activity than an identical catalyst prepared by aqueous precipitation (P). Additionally, the results indicate that the use of a non-aqueous impregnation solution as in Tests 4 and 6 provides a greater activity (145 and 159 cc/g/h, respectively) than was obtained at a much greater ruthenium level (Test 7) in which the catalyst was prepared using aqueous precipitation (114 cc/g/h). Additionally, as seen in Table III, the use of the ROR activation treatment reduces the methane yield in each case.

What is claimed is:

1. A process for the conversion of synthesis gas to a product containing liquid hydrocarbons, which comprises contacting a synthesis gas comprising hydrogen and carbon monoxide with an alumina supported cobalt-ruthenium catalyst containing from about 5 to about 30 weight percent cobalt and having a molar ratio of cobalt to ruthenium greater than about 200:1 and up to about 3400:1 under synthesis conversion conditions, said catalyst being prepared by contacting alumina with a non-aqueous, organic impregnation solution of a cobalt salt and a ruthenium salt.

2. The process of claim 1 wherein the molar ratio of cobalt to ruthenium in the catalyst is from about 250:1 to about 1000:1.

3. The process of claim 2 wherein the molar ratio of cobalt to ruthenium is from about 300:1 to about 700:1.

4. The process of claim 1 wherein said conversion process is conducted under a total pressure of at least 3.4 atmospheres.

5. The process of claim 4 wherein said process is conducted under a pressure of from about 13 to about 20 atmospheres.

6. The process of claim 1 wherein said catalyst additionally contains from about 0.1 to about 5 weight percent of a promoter metal oxide selected from the group consisting of lanthanum oxide, thoria, magnesia, and a mixture of rare earth oxides.

7. The process of claim 1 wherein said catalyst support comprises extruded alumina, wherein said alumina is gamma-alumina, eta-alumina or a mixture thereof.

8. The process of claim 1 wherein said catalyst is prepared by contacting extruded alumina with a non-aqueous, organic impregnation solution of a cobalt salt and a ruthenium salt.

9. The process of claim 8 wherein impregnation of the non-aqueous solution is conducted using the incipient wetness technique.

10. The process of claim 8 wherein said impregnated catalyst is subjected to an activation procedure comprising, in sequence, reduction in a hydrogen atmosphere, oxidation, and reduction in a hydrogen atmosphere.

11. The process of claim 10 wherein each of said reductions and oxidation are conducted while slowly heating the catalyst.

12. The process of claim 6 wherein said metal oxide is lanthanum oxide.

13. The process of claim 6 wherein said metal oxide is thoria.

14. The process of claim 6 wherein said metal oxide is magnesia.

15. A process for the conversion of synthesis gas to a product containing liquid hydrocarbons, which comprises contacting a synthesis gas comprising hydrogen and carbon monoxide with an alumina supported cobalt-ruthenium catalyst containing from about 5 to about 30 weight percent cobalt and having a molar ratio of cobalt to ruthenium greater than about 250:1 and up to about 1000:1 under synthesis conversion conditions, said catalyst being prepared by contacting an alumina support with a non-aqueous, organic impregnation solution of a cobalt salt and a ruthenium salt, said aluminum support comprising extruded alumina in the form of gamma-alumina, eta-alumina or a mixture thereof.

16. The process of claim 15 wherein said catalyst additionally contains from about 0.1 to about 5 weight percent of a promoter metal oxide selected from the group consisting of lanthanum oxide, thoria, magnesia, and a mixture of rare earth oxides.

17. The process of claim 16 wherein said promoter metal oxide is lanthanum oxide.

18. The process of claim 17 wherein said impregnation solution comprises acetone as solvent.

* * * * *